United States Patent
Rinker (10) Patent No.: US 8,733,346 B2
(45) Date of Patent: May 27, 2014

(54) SMOKE-FREE SUBSTITUTE CIGARETTE PRODUCT

(75) Inventor: Arno Rinker, Hamburg (DE)

(73) Assignee: Philip Morris Products S.A., Neuchatel (CH)

( * ) Notice: Subject to any disclaimer, the term of this patent is extended or adjusted under 35 U.S.C. 154(b) by 1223 days.

(21) Appl. No.: 12/529,807

(22) PCT Filed: Dec. 12, 2007

(86) PCT No.: PCT/EP2007/063840
§ 371 (c)(1),
(2), (4) Date: Sep. 3, 2009

(87) PCT Pub. No.: WO2008/113420
PCT Pub. Date: Sep. 25, 2008

(65) Prior Publication Data
US 2010/0126505 A1 May 27, 2010

(30) Foreign Application Priority Data
Mar. 20, 2007 (EP) .................. 07104524

(51) Int. Cl.
*A61M 15/06* (2006.01)
*A24F 47/00* (2006.01)

(52) U.S. Cl.
CPC .............. *A61M 15/06* (2013.01); *A24F 47/002* (2013.01); *A24F 47/004* (2013.01)
USPC ..................... 128/202.21; 131/194

(58) Field of Classification Search
USPC ............. 128/202.21, 202.22, 202.23, 202.24, 128/202.25, 202.26, 200.24; 131/194, 200, 131/270–273, 329, 330, 351, 900; 431/90, 431/122, 142, 143, 363; 222/3
See application file for complete search history.

(56) References Cited

U.S. PATENT DOCUMENTS 1,738,071 A * 12/1929 Johnson .......................... 431/90
2,793,504 A * 5/1957 Webster ........................ 137/322
(Continued)

FOREIGN PATENT DOCUMENTS

DE 19854008 A1 5/2008
EP 0358114 A2 3/1990
(Continued)

OTHER PUBLICATIONS

Japanese Office Action; JP Application No. 2009-553927; Mail date Aug. 21, 2012.
International Search Report PCT/EP2007/063840: Dated Apr. 29, 2008.

*Primary Examiner* — Jackie Ho
*Assistant Examiner* — Peter S Vasat
(74) *Attorney, Agent, or Firm* — Oblon, Spivak, McClelland, Maier & Neustadt, L.L.P.

(57) ABSTRACT

An aerosol-releasing inhalation device, fuelling station, and apparatus are provided. The device includes a mouthpiece having a substance depot, and a heating member detachably connected to the mouthpiece for volatilising a substance to release an inhalable aerosol. The heating member includes a housing sleeve having at least one air inlet, and at least one hot air outlet at a mouthpiece end separated from the air inlet; a filling valve at the mouthpiece end to fill a tank with a flammable gas; a premix burner; a regulating valve to control release of the gas to the premix burner by suction on the mouthpiece; and a mass transfer exchanger to heat air by heat generated from the premix burner. The substance depot at least partially passes combustion gases, and a desired inhalation air temperature is selectable by at least a proportion of the combustion gases exiting the mass transfer exchanger.

27 Claims, 7 Drawing Sheets

(56) References Cited

U.S. PATENT DOCUMENTS

| | | | |
|---|---|---|---|
| 3,631,856 A * | 1/1972 | Taylor | 128/202.21 |
| 4,938,238 A | 7/1990 | Barnes et al. | |
| 5,520,533 A * | 5/1996 | Vrolijk | 431/90 |
| 5,535,735 A | 7/1996 | Mcpherson | |
| 5,944,025 A * | 8/1999 | Cook et al. | 131/334 |
| 6,532,965 B1 * | 3/2003 | Abhulimen et al. | 131/194 |
| 6,536,442 B2 * | 3/2003 | St. Charles et al. | 131/194 |
| 2004/0031495 A1 | 2/2004 | Steinberg | |
| 2006/0014069 A1 * | 1/2006 | Kaye et al. | 429/34 |

FOREIGN PATENT DOCUMENTS

| | | |
|---|---|---|
| EP | 0858744 A1 | 8/1998 |
| WO | 8602528 A1 | 5/1986 |
| WO | 0247499 A1 | 6/2002 |
| WO | 2006082571 A1 | 8/2006 |
| WO | 2007008825 A2 | 1/2007 |

* cited by examiner

SMOKE-FREE SUBSTITUTE CIGARETTE PRODUCT

TECHNICAL FIELD OF THE INVENTION

The present invention relates in general to a method and a device for smoke-free inhalation of nicotine and additives.

BRIEF DESCRIPTION OF RELATED ART

When a conventional cigarette is smoked, tobacco is burned and the smoke arising during this combustion is inhaled (mainstream smoke) or discharged into the surrounding environment (sidestream smoke).

Mainstream smoke is the crucial factor in damaging the health of the consumer, but is what gives him/her the desired pleasure. Sidestream smoke is the crucial factor in damaging the health of passive smokers and is desired neither by the passive smokers nor by the consumer.

Over 4800 different substances have been identified in cigarette smoke, of which around 70 are demonstrably carcinogenic.

However, no serious rival to the cigarette has so far been developed. Most known products are in fact nicotine substitutes and have been developed not as products for providing pleasure but as dishabituation products.

On the other hand, known products directed purposefully at providing an alternative to the cigarette without the negative aspects thereof, are often associated with disadvantages which severely limit their acceptance by smokers.

Common to these products is the fact they do not use the heat of combustion of the tobacco, but rather other energy sources, to release a (smoke) aerosol, so largely doing away with the main source of sidestream smoke.

Devices are known whose substrates are volatilised by means of electrical energy, be it in the form of a heating resistor, an induction heater or an ultrasound atomiser, but have the disadvantage that they have, due to their size or their weight, to be held in the hand, that they are very expensive to manufacture and/or that they are difficult to dispose of in an environmentally friendly fashion due to their (heavy metal) constituents.

Products have also been conceived whose energy is obtained from combustible carbon-containing solids, such as cellulose foams, charcoal, etc. The disadvantage here is generally that sidestream smoke arises, albeit in smaller quantities and in principle with a lower harmful substance loading than in the case of conventional cigarettes or (small) cigars.

BRIEF SUMMARY OF THE INVENTION

The invention enables the user to imitate as completely as possible the act of smoking a normal cigarette. A method and a device based on this method are to be developed for this purpose. In terms of size and weight, the haptic perception of the device in both the hand and mouth should be very similar to that of a cigarette or (small) cigar. Handling and costs of the device ought not to be very different from consuming conventional cigarettes or (small) cigars.

More particularly, the invention provides a method for volatilising active and/or aroma substances for the purpose of releasing an inhalable aerosol, wherein combustion gases of a flammable gas, which is preferably substantially combusted with an excess of air, are passed partially or entirely, optionally mixed with ambient air, through an active and/or aroma substance depot and wherein a desired temperature is selectable by the proportion of combustion gases and optionally by the mixing ratio of said combustion gases with ambient air.

Such a method, preferably for inhaling a nicotine-aroma mixture, is enabled by clean combustion of an air-gas mixture, i.e. the waste gases consist of nitrogen, carbon dioxide, which is not harmful to health, water and optionally residual oxygen and may accordingly be inhaled without risk. In contrast with methods in which heat is transferred to the air solely by means of heat exchangers, the advantage of such a method is that, due to the principle on which it is based, a device for implementing this method can be embodied with very much smaller dimensions combined with higher efficiency and lower manufacturing costs.

In a further configuration, the setting of the proportion of combustion gases or the mixture ratios of these combustion gases with ambient air is established by regulating the mass flow of flammable gas, wherein regulation of the mass flow of flammable gas is preferably effected by means of a reduced pressure and/or stream of air generated by suction.

The described method is carried out with a device according to the invention with the aim of imitating the act of smoking a cigarette as completely as possible, comprising a mouthpiece (3), preferably similar in shape and dimensions to the filter including band of a cigarette or small cigar, containing an active and/or aroma substance depot (32), a heating member (2) for providing hot waste gas, preferably similar in shape and dimensions to the tobacco strand of a cigarette or a (small) cigar, comprising a housing sleeve (20) with one or more air inlets and one or more hot air outlets at the mouthpiece end, a filling valve (21) for filling of a miniature gas tank (22) with a flammable gas, preferably propane or butane gas, a regulating valve (24) for controlled release of the gas from the miniature gas tank (22) to a burner, for example a premix burner (25) for combusting the flammable gas preferably substantially with an excess of air and a mass transfer exchanger (26) for heating the air by the heat generated by means of the premix burner (25), wherein the mouthpiece (3) is detachably connected to the heating member (2), similar in shape and dimensions to a cigarette or cigar, for release of an inhalable aerosol, and control of the burner (25) is effected by the regulating valve (24) by means of the reduced pressure and/or stream of air generated by a user's suction on the mouthpiece (3).

The waste gases from the burner (25), partially or entirely mixed with ambient air, are here passed through the mouthpiece (3) in order, by means of the hot air generated in this manner, to vaporise the substances located in the active and/or aroma substance depot (32), for example so that they can be inhaled as an aerosol.

The advantages of such a method and a device based thereon are many and varied. Firstly, there is no smoke nuisance caused by combusting complex substances, such as tobacco, and secondly, due to the extremely clean combustion of a flammable gas, no "sidestream smoke" is produced, whereby third parties are not harmed by passive smoking. Thirdly, because, in contrast with a conventional cigarette, the active and/or aroma substances and the number thereof may be selected purposefully, inhalation thereof is far less harmful to health than in the case of a normal cigarette and a carcinogenic action can be purposefully ruled out. In other words, since no combustion in the conventional sense occurs, it is possible to obtain a controlled aerosol composition without causing a nuisance to third parties.

This advantage, which is vital to user acceptance, is achieved by the volatilisation of the active and/or aroma substances (formation of an inhalable aerosol) solely by the heated air from the mass transfer exchanger, i.e. without heating, let alone combusting, the depot by direct contact with the energy source. For the purposes of the present invention, an inhalable aerosol is here in principle a mixture of solid and/or liquid suspended particles and air. The inhalable aerosol preferably comprises a mist, i.e. a mixture mainly consisting of liquid suspended particles and air, preferably as far as possible free of fine dust.

In contrast to known methods, which are based on an electrical energy source for aerosol formation, the method according to the invention and the device based thereon do not require a high power storage battery, so permitting lower manufacturing costs and causing considerably fewer disposal problems.

Furthermore, flammable gas, i.e. for example "lighter gas", preferably propane and/or butane gas, as the energy source provides a further advantage of the invention, since it combines good calorific values and excellent environmental compatibility. In addition, selecting this energy source makes it possible to exploit existing infrastructure and experience, so considerably reducing manufacturing costs.

Furthermore, the shape and dimensions of the combined parts of the device, the heating member (2) and mouthpiece (3), permit use which is very similar to a conventional cigarette. In this context, the phrase "shape and dimensions of a cigarette or cigar" means that the combined parts of the device, the heating member (2) and mouthpiece (3), are of an essentially cylindrical shape and have a diameter of between approx. 6 and approx. 14 mm, preferably between approx. 8 and 11 mm and a length of approx. 50 to approx. 150 mm, preferably between approx. 75 and approx. 105 mm. Ease of handling by the user is moreover assisted by a weight which is very low in comparison with known devices, such that the device can also straightforwardly be carried in the mouth without having to be held permanently in the hand.

The small dimensions of the heating member (2), which are essential for imitating the act of smoking conventional cigarettes or (small) cigars, are only possible because the miniature gas tank (22) in the heating member (2) is limited in its volume to one consumption unit and no ignition function for the premix burner (25) is provided in the heating member (2). Reusability of the heating member (2), which is required for the purposes of the invention, is ensured by the provision of a fuelling station (1) with the functions of refilling the heating member (2) with liquefied gas and of igniting the heating member (2) which completes the device.

The similarities to handling a cigarette are additionally reinforced in that lighting the device according to the invention (i.e. starting combustion or beginning the act of smoking) is effected by the user's sucking the device and simultaneously holding the end remote from the mouthpiece to a flame, which is normally provided by the fuelling station (alternatively, however, a conventional lighter or even a match may be used).

In contrast to known products, no manual switch is necessary to start the energy source and, thanks to the selection of flammable gas, with its elevated calorific value, as the energy source, one gas tankful is sufficient for the consumption period for a conventional cigarette. Once a tankful has been consumed, the burner automatically extinguishes itself, preventing the user from forgetting to turn the device off and so enhancing safety. Before each further consumption, the heating member must be refilled again in the fuelling station.

This procedure, which is very similar to lighting a cigarette, is enabled by a regulating valve (24) which only releases sufficient gas for ignition to the premix burner (25) once the user draws on the mouthpiece (2) of the device.

The regulating valve (24) is controllable by means of a reduced pressure and/or stream of air generated by a user's suction. The valve here comprises a regulating member and means for producing a restoring force (241), wherein the regulating member comprises a first minimally open state and a second open state, wherein the regulating member may be displaced by means of the generated reduced pressure and/or stream of air against a restoring force from the first minimally open state into the second open state and the means for producing a restoring force are selected such that they are capable of returning the regulating member to the first minimally open state.

The advantage of such a valve is that it is possible, for example in the case of regulating a flammable gas, to provide at least two fundamental modes of operation: operational flame (open) and pilot flame (minimally open).

Furthermore, as soon as the user generates a sufficient reduced pressure and/or stream of air within the device, the regulating member is consequently moved into an open state and the gas can escape. If the gas is simultaneously ignited by the user, it combusts in the burner.

Regulation by a stream of air is in principle achieved by arranging obstructions to flow on the regulating member which are located in the air channel and are consequently actuated by means of the stream of air generated by suction. Regulation by reduced pressure is achieved when the pressure difference upstream and downstream of the valve body which arises due to suction is used to displace the latter. The two regulation options may, of course, be combined. A sufficient stream of air may for example be deemed to be a volumetric flow rate of between 15 and 20 ml/s, typically of approx. 17.5 ml/s. A corresponding reduced pressure amounts for example to between 50 and 500 mbar, preferably between 100 and 200 mbar.

So that the flow rate can be regulated, on opening of the valve by suction, means for producing a restoring force (241), for example a spring, are tensioned.

When the user stops drawing on the mouthpiece, the regulating member is pushed back by this restoring force.

Accordingly, in this context, "minimally open" or the corresponding phrases "minimal flow rate" or "minimal flow section" should be taken to mean a state in which a small quantity of gas flows which is just sufficient for the flame in a downstream burner not to go out. The resultant operating state, also known as pilot flame, allows the user to take a number of draws without each time having to relight the burner, while consuming the least possible gas, which is of benefit to a more compact structure, as with the device according to the invention.

In the second open state, the regulating member preferably opens a flow section which, depending on the reduced pressure and/or stream of air, is variably controllable between a minimally open and a fully open state, so permitting finer regulation depending on the user's strength of suction or his/her smoking habits.

In a further configuration of this device, the latter additionally comprises a main valve (23) between the miniature gas tank (22) and regulating valve (24) which is opened by connecting the mouthpiece (3) to the heating member (2) and is closed again by detaching the mouthpiece (3). This ensures that no gas can escape when the device is not ready for operation, i.e. when the mouthpiece is not fitted to the heating member.

In a further configuration, the regulator (24) may assume a further, third closed state after separation of the heating member (2) and mouthpiece (3), which state is maintained when a mouthpiece is again fitted until the regulating member is exposed to a reduced pressure and/or stream of air which, on exceeding a minimum value, displaces the regulating member into the minimally open state, the open state or a state between minimally open and open.

This third closed state makes it possible to store a heating member (2) which has been provided with a new mouthpiece (3) and fuelled, or for example to hold it in the hand, until it is desired to start smoking, i.e. until the desired time of igniting the heating member, without gas escaping.

The premix burner (25) of the heating member (2) is preferably a liquefied gas premix burner, i.e. the flammable mixture is formed before it emerges from the nozzle, such that complete combustion of the liquefied gas is ensured. This type of burner includes, for example, Nainen, Ikari, matrix or catalytic burners, some of which are known from storm lighters and small manual gas-fuelled soldering irons.

The similarity to a conventional cigarette during use may furthermore be completed by a glow occurring at the end remote from the mouthpiece as soon as the user draws on the mouthpiece. This is achieved, for example, by a metal mesh which is arranged in the flame or flame front. With each draw on the device, the larger and hotter operational flame causes the mesh to glow. The mesh should here be highly heat resistant, i.e. should not burn up at the temperatures reached in the flame, for example such a mesh may consist of tungsten or a tungsten alloy.

In a preferred configuration of the burner (25) as a catalytic burner, the glow mesh optionally simultaneously acts as a support for a catalyst, such as for example platinum or palladium.

Since very high temperatures may sometimes be reached in operation, it may be advisable to provide an overheating safety device, for example a bimetallic thermostat. This may be constructed such that, on extension in the event of overheating, it closes the regulating valve and interrupts the supply of gas to the burner. This may for example proceed by its extension permitting the regulating valve to enter an additional (fourth) state in which the regulating valve is closed or by its pushing the regulating valve back into the third state. Both may be achieved in that the means for producing a restoring force (241), for example a spring, is acted upon, for example by displacement of the spring excursion, such that said means can place the valve in a fourth closed position or, alternatively, in its third closed position.

The air which is required for volatilising the substances present in the depot is heated according to the invention by a "mass transfer exchanger" (26). Since a temperature increase of the inhalation air of for example at least 180° C. is necessary if the inhalation air is still to have a temperature of 100° C. on leaving the depot, the heating member (2) preferably comprises a mass transfer exchanger (26) in which the waste gases from combustion of the flammable gas are used at least in part as hot air, wherein fresh air may be mixed therewith to establish the required temperature. For example 3 to 100%, preferably 5 to 50% of the waste gases may accordingly be introduced into the hot air stream.

Due to the compact dimensions of a device according to the invention, said device is preferably constructed such that one or more of the hot air channels (27) leading to the hot air outlet(s) are arranged coaxially around the gas tank (21) of the heating member (2). These hot air channels (27) guide the heated air from the mass transfer exchanger (25) to the hot air outlets, where, when a mouthpiece is fitted, the heated air is guided to the user's mouth through the chamber or chambers of the depot (32) for the purpose of volatilising the active and aroma substances present therein.

Consumption preferably results in stimulation of the taste buds and of the nicotine receptors. In a preferred embodiment, the device accordingly contains in the active and/or aroma substance depot (32) nicotine as the active substance and optionally aroma substances, and optionally further additives and auxiliaries, such as irritants, for example capsaicin, stabilisers, for example propylene glycol, volatilisation aids, for example ethanol, etc.

In a depot (32) comprising a plurality of ingredients it may be advantageous or necessary, for example due to the different energies of vaporisation which are required, for the active substance(s), optional aroma substance(s) and optional further additives and auxiliaries to be present individually and/or mixed in a plurality of chambers. The chambers may here have different characteristics with regard to dimensions and shape in order to achieve the desired dosage of the individual components, for example by varying the flow section and/or the depot materials, etc.

Since the above-stated gases, such as butane and/or propane, when combusted stoichiometrically, i.e. with a $\lambda_{air}$ value (air ratio) of $\geq 1$, react completely to yield carbon dioxide ($CO_2$) and water ($H_2O$), the combustion waste gas is clean from a health standpoint. Nevertheless, even in the case of combustion operating substantially with an excess of air, it may happen, especially in the event of load change responses, that this $\lambda_{air}$ value is temporarily less than 1, i.e. combustion is in part incomplete, which in practice in the case of a mass transfer exchanger, i.e. when a proportion of the waste gases are directly used for heating by mixing with ambient air, would result in small quantities of carbon monoxide (CO) in the inhaled air.

A further embodiment of the device accordingly provides that a carbon monoxide oxidation catalyst, for example a hopcalite catalyst, is arranged downstream of the mass transfer exchanger (26), whereby any small quantities of carbon monoxide are converted into harmless carbon dioxide ($CO_2$).

A further aspect of the invention is the provision of a fuelling station (1) for detachable connection and filling of the heating member (2) of a device according to the invention, which comprises a gas storage tank (11), the volume of which is a multiple of the volume of the miniature gas tank (22) of the heating member (2), for example at least 100 times, preferably at least the 200 times the volume, and an outlet valve (17) connectable by form-fit and/or force-fit and in gas-tight manner to the filling valve (21) of the heating member.

This allows the user to fill the reusable heating member (2) with flammable gas after removal (or before fitting) of the mouthpiece (3). Without a fuelling station (1), it is not possible completely to achieve the invention which inter alia requires that there be no major difference in handling and costs of the device according to the invention relative to the consumption of conventional cigarettes or (small) cigars.

The fuelling station (1) preferably not only serves the purpose of filling the heating member (2), but also of storing it when it is not being used. In a further embodiment, the fuelling station (1) therefore furthermore comprises means for storing a heating member with a storage cavity (18) which at least partially encloses the filling valve (17) for accommodating a mouthpiece-end part of the heating member (2) together with a movable lid (19) which in a closed position covers the opposing end of the heating member (2). Since this lid (19)

covers the optionally still hot end of the heating member (2), it is preferably constructed as a heat shield, for example from a heat-resistant and preferably insulating material, so that the user can without risk immediately place the fuelling station (1) with an inserted heating member (2) for example into his/her pocket.

In a further configuration, the fuelling station (1) additionally contains an ignition device (163), for example a piezo igniter, with which the device comprising heating member (2) and mouthpiece (3) may be ignited.

In a further preferred configuration, in addition to such an ignition device (163), the fuelling station (1) furthermore preferably comprises a burner valve (162) and a burner (164), for example a diffusion burner, a partial premix burner or preferably a premix burner, wherein in such a case the burner valve (162), the ignition device (163) and the burner (164) constitute a complete lighter which primarily serves to ignite the device (heating member) and secondarily, independently of the heating member (2), may be used as a conventional lighter.

Due to the scant structural space which is available, the miniature gas tank (22) of the heating member must be completely filled before each consumption with liquefied gas, at least 90% of which, preferably 100% of which must be present in the liquid phase, in order to be able to operate the burner (25) over the required consumption period. The fuelling station (1) should, preferably for reasons of the required simple handling, fill the heating member (2) with liquefied gas after insertion into the storage cavity (18) without the user being instructed.

In order to achieve this, with the refill valves (17, 21) of fuelling station (1) and heating member (2) connected and open, a pressure must always prevail on the fuelling station side until the gas storage tank (11) of the fuelling station (1) is virtually completely empty which is above the vapour pressure necessary for liquefaction of the liquefied gas. This guarantees that, irrespective of the spatial position of the fuelling station (1), filling of the heating member (2) with liquefied gas is ensured.

This is achieved by a fuelling station (1) with a gas storage tank (11), which is subdivided by a piston (12), which is axially mobile along an adjustment path, into a first chamber (13) filled with an inert gas, preferably nitrogen, and a second chamber (14) filled with a flammable gas, preferably propane or butane gas, wherein the pressure in the first chamber (13) filled with inert gas is sufficient over the entire adjustment path of the piston (12) to keep the gas in the chamber (14) filled with a flammable gas in the liquid phase.

When the liquefied gas chamber (14) is empty, this means that the pressurised gas chamber (13) occupies the entire space in the gas storage tank (11) and the pressure in the pressurised gas amounts for example to 3 bar if, for example, butane is provided for the liquefied gas chamber (14). If the liquefied gas chamber (14) is filled with butane, the butane is accordingly always in the liquid phase and the gas in the pressurised gas chamber (13) is compressed by the piston (12). In the stated example, if, after filling, the liquefied gas chamber (14) occupies 85% of the volume of the gas storage tank, the total pressure of the system amounts to approx. 21 bar.

In order to protect the gas storage tank (11) from inadmissible pressures, as may occur for example on exposure to direct sunlight in vehicles, the chamber (13) filled with inert gas is connected to the surrounding environment by way of a pressure relief valve (131). Since consequently no flammable liquefied gas is vented in the event of overpressure, there is no explosion hazard.

The liquefied gas chamber (14) is connected by way of a pressure reducer (15) to the outlet valve (17) and, in a variant configuration of the fuelling station (1) comprising an integral lighter (16), possibly with an interposed throttle (161), to the burner valve (162).

The pressure reducer (15) is constructed such that the back pressure is sufficient to keep the liquefied gas in the liquid phase in the upstream system. Accordingly, each time the heating member (2) is refueled, this ensures that the latter is, on the one hand, always completely filled with liquefied gas and, on the other hand, neither the heating member (2) nor the burner valve (162) [is exposed] to an excessively elevated pressure, as occurs in the gas storage tank (11) if the liquefied gas chamber (14) is not completely emptied.

Although the fuelling station (1) may be designed as a disposable product, it is advantageous for it furthermore to comprise a filling valve (141) for filling the gas storage tank (11) which makes it possible to refill it and make further use of it once the storage tank has been emptied.

The invention obviously also relates to the individual components, i.e. the reusable heating member (2), the disposable mouthpiece (3) and the associated fuelling station (1). The invention preferably also relates to a kit comprising a fuelling station and a heating member as described above, optionally with a plurality of mouthpieces.

Only by using all three components is it possible to provide a device which achieves the invention of imitating the act of smoking as completely as possible.

The following advantageous characteristics may be achieved by the proposed device:
  Cigarette-like appearance (heating member with mouthpiece)
  Nicotine emitted in the mainstream, as in a cigarette
  Taste experience as when smoking a cigarette
  Slight scratching or burning in the mouth and throat, as when smoking a cigarette
  Handling similar to a cigarette
  Low manufacturing costs, so low sales price for fuelling station and heating member, preferably sales price of <10 €
  At least 50%, preferably at least 95% reduction in harmful substances in the sidestream relative to a conventional cigarette (waste gas: only air+water and $CO_2$)
  At least 20%, preferably at least 50%, depending on ingredient selection, even at least 90% reduction in harmful substances in the mainstream relative to a conventional cigarette (waste gas (+air)+for example nicotine and aromas)
  Purposeful exclusion of substances possibly harmful to health, for example carcinogens, and possibility of purposeful dosage of ingredients and emissions below admissible limit values.

BRIEF DESCRIPTION OF THE FIGURES

Certain configurations of the invention will now be described below with reference to the attached Figures.

FIG. 1 is a schematic representation of the method in the form of a flowchart. The parallelograms represent the substances involved in the method, while the rectangles show the sub-processes of the method. The thin arrows symbolise the flow caused by the kinetics of the liquefied gas, while the thick arrows show the stream of air caused by suction. The broken line represents the influence of the reduced pressure and/or stream of air on the mass flow rate of the liquefied gas.

Further details and advantages of the invention may be inferred from the following detailed description of possible embodiments of the invention made with reference to the attached Figures.

DETAILED DESCRIPTION OF THE INVENTION

1. Configurations of the Fuelling Station 1 (See FIGS. 1 and 2)

Figure 1:
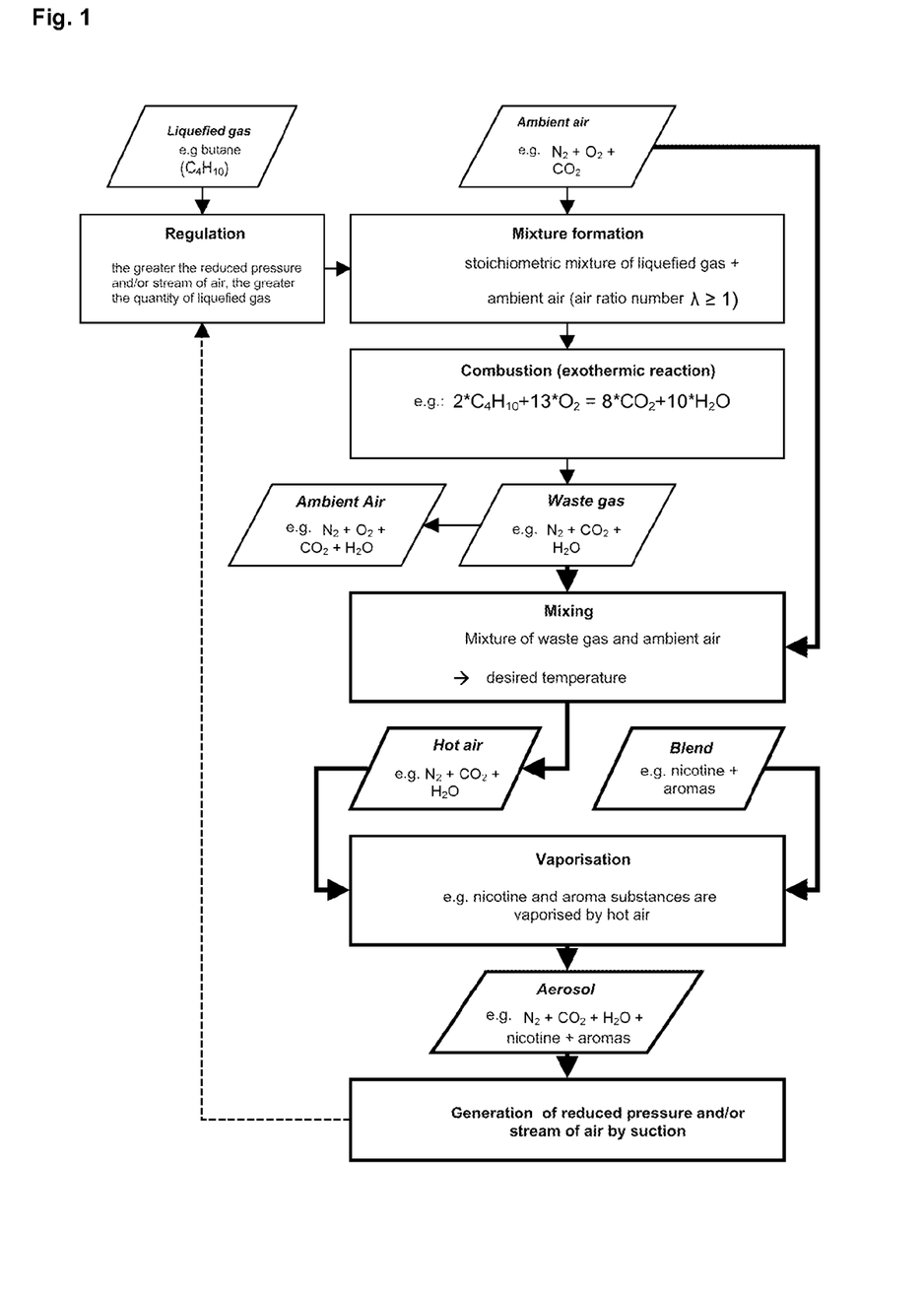
Figure 2:
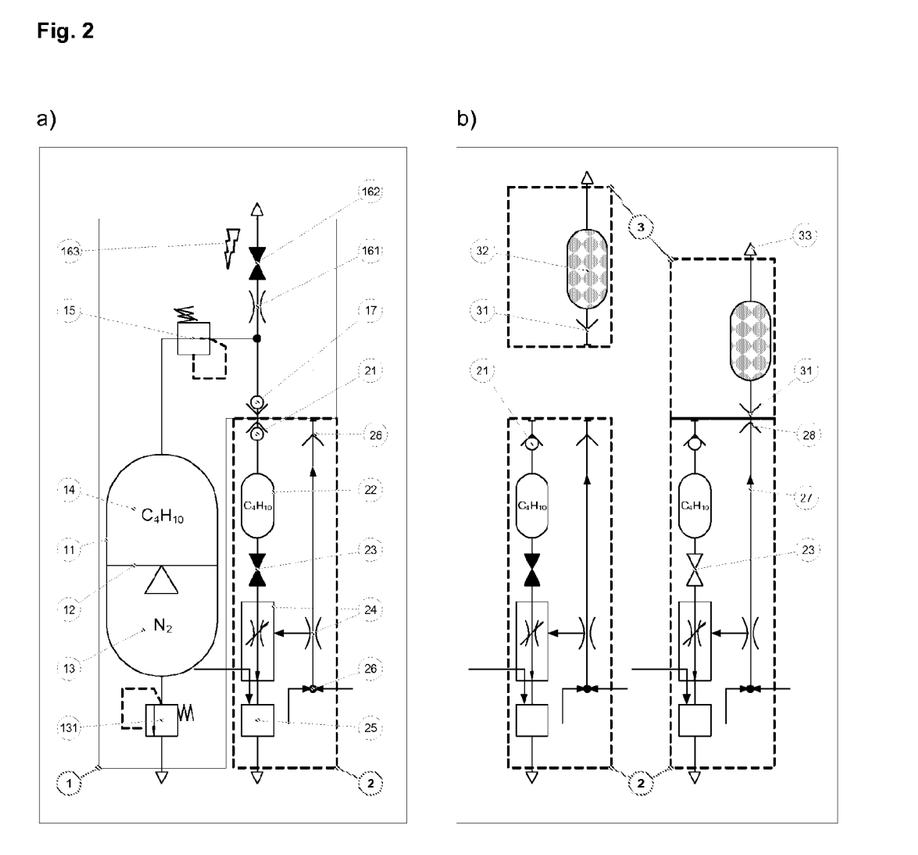
FIG. 2 contains schematic representations of the device components, fuelling station 1, heating member 2 and mouthpiece 3.
- a) shows the heating member 2 inserted into the fuelling station 1. The refill valves 17 and 21 are open, whereby the heating member 2 is filled.
- b) shows how a mouthpiece 3 is screwed on to the heating member 2 by connecting the bayonet closure parts 27 and 31, whereby the main valve 23 of the heating member 2 is opened.

The fuelling station 1 serves in principle for refueling, optionally also for storing and igniting the heating member 2. With the (inserted) heating member, it forms the transportable hardware of the product. In one preferred configuration, it is an enhanced lighter, which may accommodate and fuel the heating member 2 according to the invention.

1.1 Configuration T1 of a Fuelling Station

In a first configuration the fuelling station 1 serves solely for refueling the heating member 2 and consists therefore only of a gas storage tank 11 with refill valve 141 for refilling the fuelling station 1 and an outlet valve 17 for refilling the heating member 2. Preferably, the heating member 2 may remain in the fuelling station 1 for storage purposes when not in use. To ignite the heating member 2, it is necessary for either an igniter to be accommodated in the heating member (increased amount of space required in the heating member) or an additional lighter to be used.

1.2 Configuration T2 of a Fuelling Station with Igniter

As configuration T1, but additionally comprising an integral ignition mechanism 163 for igniting the heating member 2. Unlike in configuration T1, however, there is no need for an additional lighter (no requirement for increased space in the heating member or in the consumer's pocket).

1.3 Configuration T3 of a Fuelling Station with Lighter

As configuration T1, but additionally comprising an integral lighter 16 for igniting the heating member 2. For instance, the fuelling station 1 may also be used as a conventional lighter, which is of benefit in particular to those customers who would like, in addition to the smoke-free cigarette, also to consume conventional cigarettes or small cigars.

1.3.1 Fuelling Station T3 in Detail (cf. FIGS. 1 and 2)

1.3.1.1 Gas Storage Tank

From the point of view of structural space, the gas storage tank 11 is the largest component of the fuelling station 1 and the energy source of the entire smoke-free cigarette system. The liquefied gas tank 11 refillable with conventional lighter gas supplies
- the lighter 16 incorporated into the fuelling station 1,
- the heating member 2 in the heating member receptacle 18, if the multifunctional lid 19 is pressed or closed with the heating member 2 inserted therein.

The gas storage tank 11 is subdivided by an axially mobile, gas-tight piston 12 into a nitrogen chamber 13 and a butane chamber 14. If the butane chamber 14 is empty, the nitrogen chamber 13 and the piston 12 occupy the entire structural space within the gas storage tank 11. In this situation, the pressure in the nitrogen chamber 13 is only just above the vapour pressure of butane, i.e. above the pressure needed to liquefy butane at room temperature. If the butane chamber 14 is full, the butane, which is liquid and incompressible due to the pressure prevailing in the nitrogen chamber 13, moves the piston 12, whereby the butane chamber 14 becomes larger and the nitrogen chamber 13 smaller. The pressure in the two chambers rises due to the compression of the nitrogen and is thereby above the vapour pressure of butane whatever the filling level of the butane chamber 14, whereby the butane chamber 14 is always filled 100% with liquid butane.

In order to safeguard the gas storage tank 11 against pressures which would result in destruction of the tank, the nitrogen chamber 13 is connected to the surrounding environment by way of a pressure relief valve 131. If the pressure in the gas storage tank 11 climbs to above a permissible value, the valve opens and discharges nitrogen into the surrounding environment, until the pressure in the liquefied gas tank 11 is once again below the permissible maximum value. This arrangement on the one hand prevents the tank from exploding and possibly injuring people and on the other hand prevents butane from escaping undesirably.

The butane chamber 14 is connected to the integral lighter 16 and the heating member filling valve 17 by way of a pressure reducer 15. The pressure reducer 15 is designed such that the heating member 1 is always filled at a pressure which keeps the butane in the liquid phase, so ensuring maximum filling of the miniature gas tank 22 in the heating member 2. The back pressure of the pressure reducer 15 is just above the vapour pressure of butane and protects the integral lighter 16 and the outlet valve 17 from pressures which are too high for these components, as are present within the gas storage tank 11 over almost the entire life cycle of the fuelling station 1.

1.3.1.2 Integral Lighter

The integral lighter 16 is for example a premix burner with piezo ignition, as is known with conventional commercial storm lighters. The lighter 16 serves to ignite the heating member 2. In addition, it may also be used as a conventional lighter.

1.3.1.3 Multifunctional Lid

The lid 19 of the fuelling station 1 is configured in such a way, due to its shape and kinematics, that it fulfils four different functions: fuelling the heating member, locking the heating member in place, providing a heat shield for the heating member burner and turning on the lighter. In principle, all the functions of the multifunctional lid may be fulfilled by a plurality of components in the widest range of variants. The "multifunctional lid" approach is however preferred as the most elegant and probably most cost-effective due to the high level of integration of functions.

Therefore at this point all four functions are assumed by the lid.

Function 1: Fuelling the heating member 2: When closed, the lid 19 encloses the tip of the heating member 2, whereby the heating member 2 is pressed into its receptacle 18, such that the valve 17 of the fuelling station 1 at the bottom of the receptacle is pressed in gas-tight manner onto the inlet valve 21 of the heating member 2. As a result of this contact pressure, the two valves open and the heating member 2 is filled with gas by the fuelling station 1 until the pressure between fuelling station 1 and heating member 2 is equalised or the lid 18 is opened. Pressure equalisation is preferably accompanied by a hissing noise. When the noise stops, the heating member is fully fuelled.

Function 2: Locking the heating member 2 in place: The latching mechanism of the lid 19 is designed such that it snaps in or out, depending on its previous state, with or without an inserted heating member 2 by pressing down in the fuelling position. With the heating member 2 inserted, the heating member 2 is fuelled by pressing down on the lid 19.

Function 3: Heat shield for burner: The lid 19 is such that it is pushed and/or folded over the end of the heating member 2 which is hot after use (burner tip). It forms heat protection, which prevents contact with the burner tip of the heating member 2 when the lid 19 is closed. In addition, it is designed with regard to its heat-conducting properties such that on the one hand the burner tip may cool as quickly as possible and on the other hand no temperature which is unpleasant for people arises on the outside of the lid.

Function 4: Turning on the lighter: In the fully open state the lighter incorporated into the fuelling station 1 is actuated by pressing down on the multifunctional lid 19, i.e. the gas supply is opened up and the igniter 163 of the lighter 16 is actuated in one movement.

1.3.1.4 Heating Member Receptacle

The receptacle 18 for the heating member 2 is preferably such that the heating member 2 may only be inserted when its mouthpiece end does not have a mouthpiece 3 positioned thereon.

1.3.1.5 Outlet Valve

At the bottom of the receptacle 18 is located the outlet valve 17 of the fuelling station 1, which valve is connected in gas-tight manner with the heating member 2, when the latter is inserted, for example by pressing on or closing the multifunctional lid 18. The outlet valve 17 is preferably such that, when pressed down, it opens itself and the inlet valve 21 of the heating member 2, such that gas may flow out of the fuelling station 1 into the heating member 2.

2. Heating Member (cf. FIGS. 1, 2 and 3)

Figure 3:
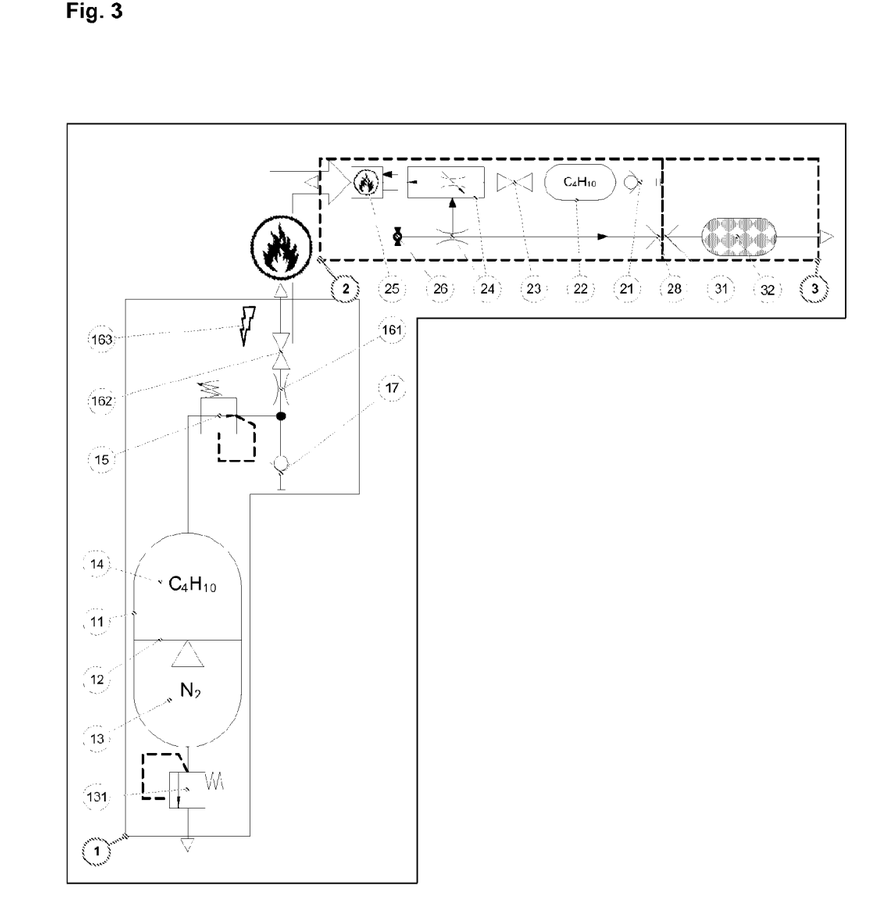
FIG. 3 is a schematic representation of the device components and shows how the screwed-together components, heating member 2 and mouthpiece 3, are ignited with the assistance of the fuelling station 1.
Figure 4:
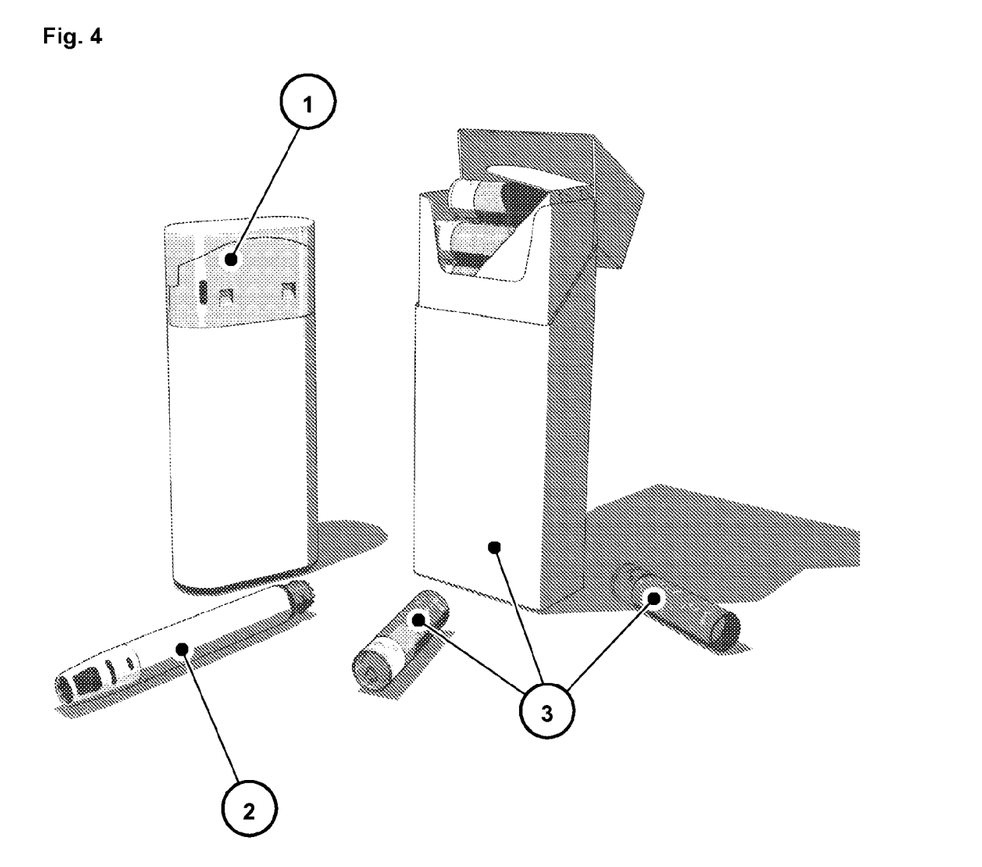
FIG. 4 shows a perspective view of the three components belonging to the device, fuelling station 1, heating member 2 and mouthpiece 3, and a packet with mouthpieces 3.

It is common to the following heating member configurations that they heat air to form an aerosol enriched with nicotine and aromas by combusting liquefied gas. The dimensions of the heating member 2 should not significantly exceed those of a conventional cigarette (without filter).

A mass transfer exchanger 26 is connected downstream of the burner 25, i.e. ambient air is mixed with hot waste gas. The mixing ratio and thus the inhalation air temperature at the mass transfer exchanger output depends on the design of the mass transfer exchanger 26 (ratio of the inflow sections:mass transfer exchanger waste gas inlet 262 to mass transfer exchanger air inlet 261).

2.1 Preferred Heating Member Concept in Detail

2.1.1 Sleeve

The sleeve 20 of the heating member 2 may consist of one or more cylindrical parts. The outside of the sleeve 20 lends the heating member 2 its cigarette-like appearance and forms the holding surface for the consumer. It is the main component carrier of the heating member 2. At the level of the miniature gas tank 22 the sleeve 20 is shaped inside in such a way that, on the one hand, hot air channels 27 arise between sleeve 20 and miniature gas tank 22 and, on the other hand, the miniature gas tank 22 is axially displaceable therein. At the mouthpiece end, the miniature gas tank 22 has a limit stop for its axial movement through the sleeve 20. In the filling port 220 of the miniature gas tank 22 a bore 221 is provided, which on the one hand allows introduction of the heating member filling valve of the fuelling station 17 as far as the heating member filling valve of the heating member 21 and on the other hand forms a flow channel. Small air flow openings 222 are provided in a ring radially around this bore 221, which connect the hot air channels 27 arranged around the miniature gas tank 22 with the bore 221 in the filling port 220. A seal 201 is applied to the outer surface of the sleeve 20 at the mouthpiece end, which seal prevents outside air from flowing in while a mouthpiece 3 is being screwed onto the bayonet coupling of the miniature gas tank 28, such that, on sucking on the screwed-on or pushed-on mouthpiece 3, the air has to be guided through the heating member 2.

The sleeve 20 is a component carrier and preferably a functional partner for the following further assemblies and components:
 a. control valve 24
 b. burner 25

2.1.2 Miniature Gas Tank

The miniature gas tank 22 is the energy source for the burner 25 in the heating member 2 and is dimensioned such that the liquefied gas stored therein is sufficient for consumption of a mouthpiece 3. The duration of mouthpiece consumption is intended to resemble as closely as possible the consumption of a cigarette, i.e. 3-5 min depending on use. At its mouthpiece end there is located the heating member filling valve 21 for fuelling the heating member 2 by means of the fuelling station 1. This end is for example a filling port 220, which forms a bayonet joint with the mouthpiece 3. The miniature gas tank 22 is accommodated in the heating member 2 in an axially mobile manner, such that when screwing/pushing on a mouthpiece 3 the tank 22 is moved towards the mouthpiece 3. The main valve 23 is accommodated at the burner end of the miniature gas tank 22, optionally with an interposed pressure reducer. The main valve 23 corresponds in principle to a conventional outlet valve of a lighter. In contrast to the lighter, however, the valve is not actuated by fixing the tank and pulling on the valve nozzle but rather by holding the valve nozzle and pulling on the tank 22. If therefore a mouthpiece 3 is screwed onto the heating member 2, the main valve 23 releases gas feed from the tank 22 to the regulating valve 24. Between the tank 22 and the mouthpiece end of the sleeve 20 a small spring element 223 may additionally be fitted, if the main valve 23 does not have sufficient force to pull back the tank 22 and thus for closure when the mouthpiece is removed.

Figure 5:
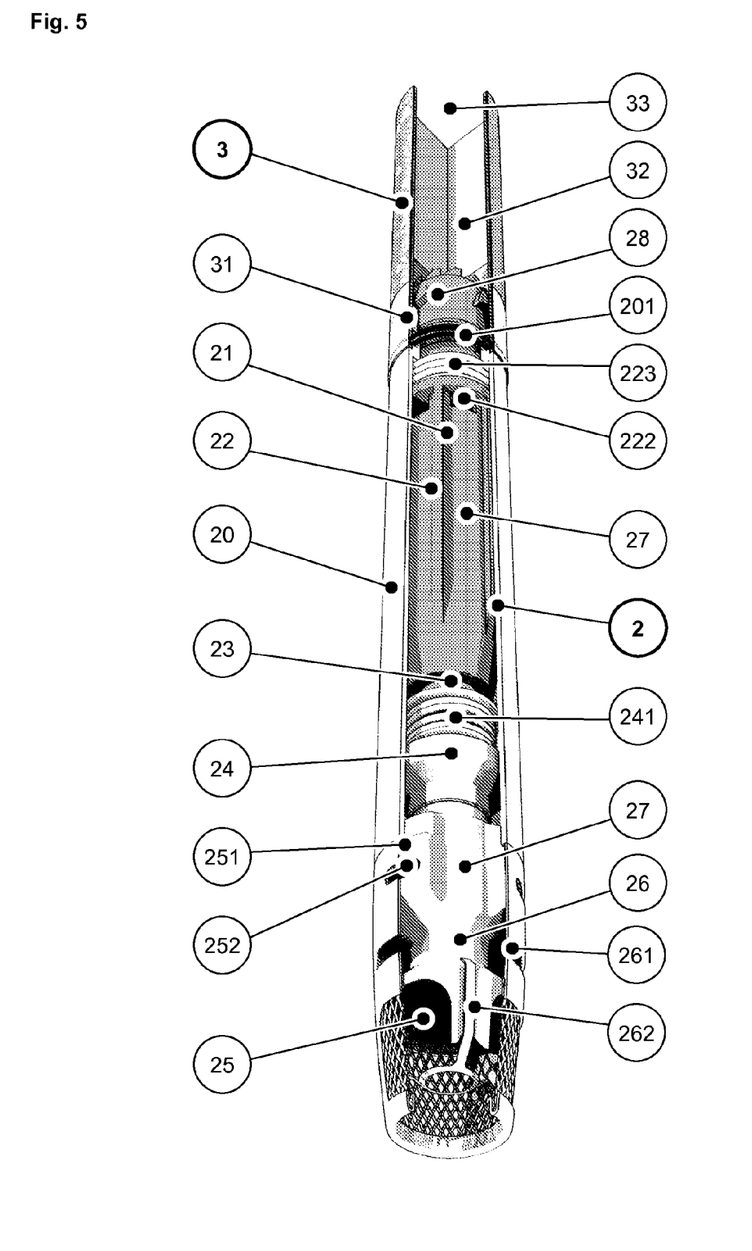
FIG. 5 shows a perspective sectional view of the heating member 2 with screwed-on mouthpiece 3.
Figure 6:
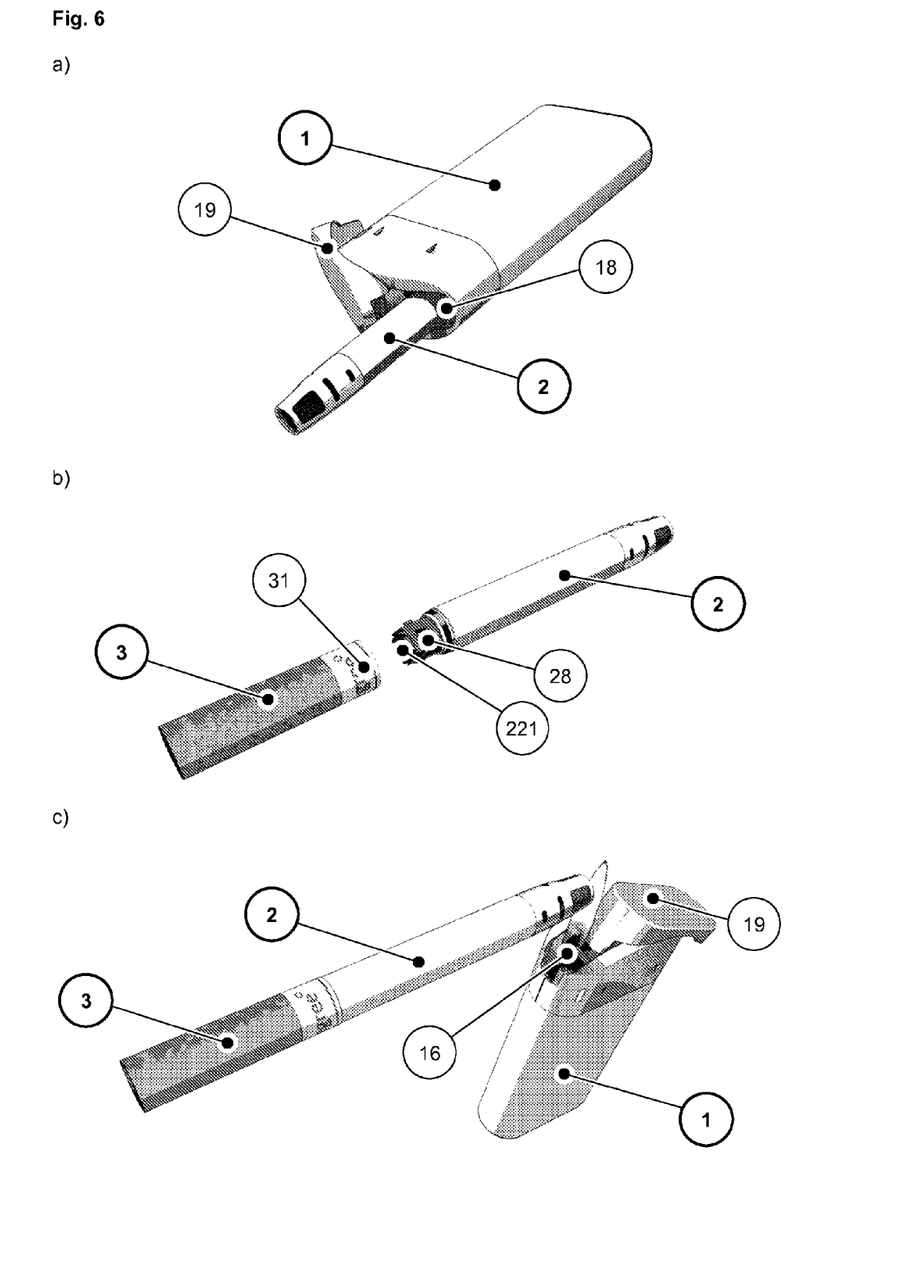
FIG. 6 shows a perspective view of an embodiment a) of a fuelling station 1 with open lid 19 and heating member 2 being removed from the fuelling station 1, b) of a mouthpiece 3 before it is screwed onto the heating member 2 and c) a heating member 2 with mouthpiece 3 positioned thereon during ignition by the fuelling station 1.

2.1.3 Regulating Valve (See FIGS. 2, 3 and 5)

The regulating valve 24 controls the gas and air supply for the burner 25 as a function of the flow of inhalation air within the sleeve 20. It is arranged so as to be axially movable on the central part of the nozzle between the main valve 23 of the miniature gas tank 22 and the burner 25. Externally the regulating valve 24 forms a narrow gap with the sleeve 20. In the radial direction the regulating valve 24 is provided for example with small notches on the inside to regulate the gas stream.

The gap between sleeve 20 and regulating valve 24 is such that the regulating valve 24 acts for example as a throttle in the stream of air. Depending on the pressure difference up- and downstream of the valve 24, it is either drawn towards the mouthpiece 3 or pushed away therefrom. The regulating valve 24 may adopt two relevant positions with the following properties:

pilot flame: The regulating member of the regulating valve 24 is located in the standby position, whereby just enough gas passes through the valve for the flame in the burner 25 not to go out.

operational flame: The regulating member of the regulating valve 24 has been moved out of the standby position towards the mouthpiece 3 by suction thereon and now releases sufficient gas for the burner 25 to output sufficient fuel gas to heat the inhalation air. If the regulating member is moved out of the standby position towards the mouthpiece 3, it compresses a spring 241. The spring 241 is configured such that it pushes the regulating member of the valve 24 into the standby position in the absence of suction on the mouthpiece.

Different performance maps for the burner may result from different geometries of the openings on the valve 24.

2.1.4 Burner

The burner 25 is preferably a liquefied gas premix burner, i.e. the flammable mixture of gas and air flowing in through the air inlets 252 is formed in the mixing chamber 251 before it emerges from the nozzle, such that complete combustion of the liquefied gas is ensured. This type of burner includes, for example, Nainen, Ikari, matrix or catalytic burners, some of which are known from storm lighters and manual gas-fuelled soldering irons.

Typical Nainen burners have an annular opening approx. 0.5 cm above the nozzle outlet, with a "reaction mesh" which is heated by the ignition flame and brings about constant reignition of the gas flowing through. Nainen burners form above the reaction mesh a conical, short, non-luminous, blue flame, which has a diameter equal to the annular opening at its base.

To improve load change characteristics between pilot flame and operational flame, the use of a three-dimensional reaction mesh may also be provided.

Furthermore, the burner 25 is optionally equipped with an overheating safety device, for example in the form of a bimetallic thermostat, which by expansion for example controls the regulator limit stop and thus closes the regulating valve 24 on overheating.

2.1.5 Mass Transfer Exchanger

The mass transfer exchanger 26 transfers waste gas from the burner 25 to the inhalation air by way of the mass transfer exchanger waste gas inlet 262.

The mass transfer exchanger 26 is configured such that, on suction on the mouthpiece 3, waste gas is mixed with ambient air in such a way that the resultant mixture has the right temperature to detach the mixture from the mouthpiece 2. The temperature loss on throughflow of the heating member 2 must also be taken in account.

3 Consumables

Consumables include all components and substances which have to be replaced after single use. Consumables consist of the mouthpiece 3 and the mixture applied therein in a depot 32.

3.1 Mouthpiece (FIGS. 2, 3, 4, 5, 6 and 7)

The mouthpiece 3 corresponds in size approximately to a cigarette filter, but unlike the latter does not have any filter function. Unlike a filter, the mouthpiece is not intended to extract any substances from the inhalation air, but rather to add substances to the inhalation air. All parts of the mouthpiece 3 preferably consist 100% of biodegradable materials.

3.1.1 Sleeve

The one- or multipart sleeve of the mouthpiece 3 is the holding surface for the consumer and the contact surface with the mouth of the consumer. It is preferably a cylindrical gas- and liquid-tight hollow article with openings at both ends. The heating member end is shaped such that the inhalation air may flow undisturbed out of the hot air outlets 221 of the heating member 2 through the hot air inlet openings 30 into the mouthpiece 3 and that a gas-tight connection arises by screwing the mouthpiece 3 onto the heating member 2.

3.1.2 Depot

Figure 7:
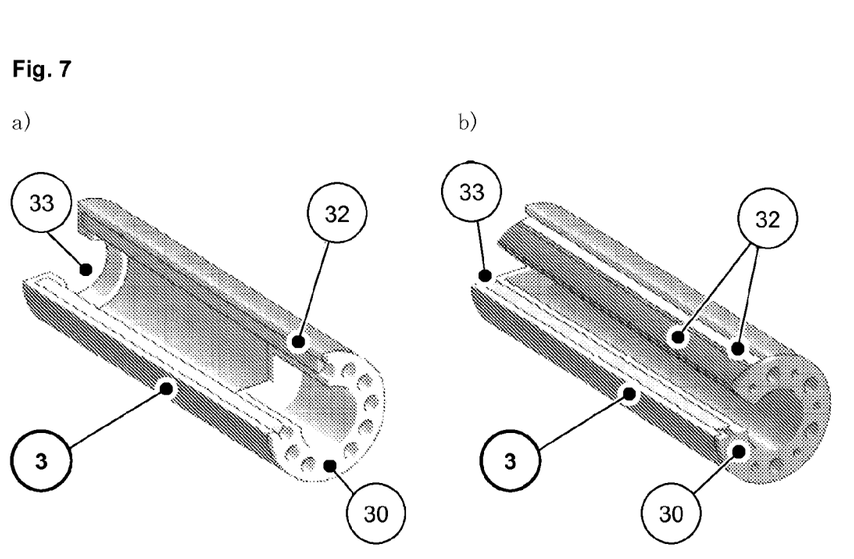
FIG. 7 shows a) a mouthpiece 3 with hot air inlet openings 30, a single-chamber depot 32 and aerosol outlet openings 33, and b) a mouthpiece 3 with a multi-chamber depot 32.

The depot 32 is arranged in principle within the sleeve coaxially therewith and serves to store the active and/or aroma substance mixture, which is also called a blend. The affinity of the depot material to the mixture has to be high enough for as good as none of the mixture to be released by the depot even under elevated temperature storage conditions. When the operating temperature is reached for the inhalation air (hot air), which flows through the mouthpiece, the depot 32 has however to release the mixture to the required extent, to arrive at the user as an aerosol by way of the aerosol outlet opening 33.

The depot 32 in the mouthpiece 3 may if required consist of a plurality of chambers (see FIG. 7*b*).

In order to take account of the differences in vaporisation temperatures of for example the aromas and nicotine, it may be necessary to accommodate these in separate depots 32 with different flow sections and/or different properties of the depot material (thermal capacity, affinity to the applied mixture etc.).

By a snapped-in position for example of the bayonet coupling 28/31 between mouthpiece 3 and heating member 2, the throughflow openings of the mouthpiece 3 and the hot air outlets 221 of the heating member 2 may be brought into the correct position.

3.1.3 Mouthpiece Sealing

For reasons of hygiene and reasons of durability and storability, the mouthpiece 3 may also be sealed. A mouthpiece seal may consist, for example, of two small gas- and liquid-tight films, which are adhesively bonded to the end faces of the mouthpiece and removed prior to use. For simple removal, the films may additionally be provided with a small tab.

3.2 Active and/or Aroma Substance Mixture

The mixture is the main constituent of smoke simulation, since it contains all the desired stimulants, which are released when a sufficient temperature is reached. Possible ingredients are divided into the following groups.

3.2.1 Active Substances

The active substances consist primarily of nicotine and the derivatives thereof, although other stimulants may be used as well or instead, for example caffeine and/or taurine. The quantity of active substance in the mixture may be metered very simply during production and could for example include less nicotine than a conventional cigarette or small cigar but release the same amount as a cigarette when the operating temperature is reached. Vitamins and minerals may additionally be added.

3.2.2 Aroma Substances or Flavours

The flavours are mainly aromas which are permitted according to the German Ordinance on Aromas. Sugar may for example also be added as a flavour.

3.2.3 Irritants

The irritants serve to imitate the "scratching" of the throat which arises during smoking. Capsaicin (produces spiciness in foodstuffs) and/or other irritants, for example, may be used in safe quantities.

Volatilisation Aids

Volatilisation aids such as ethanol, water, polyols or the like may be added for better vaporisation of the mixture.

Stabilisers

To increase storage life and/or prevent undesired reactions between the constituents of the mixture, various stabilisers may also be used.

Further Additives

Use of further additives is possible provided they are harmless to consumer health in the quantities used.

The invention claimed is:

1. An aerosol-releasing inhalation device, comprising:
a mouthpiece comprising a substance depot; and
a heating member configured to volatilise at least one substance in the substance depot to release an inhalable aerosol, the heating member comprising:
a housing sleeve having at least one air inlet, and at least one hot air outlet at a mouthpiece end of the housing sleeve being separated from the at least one air inlet;
a filling valve at the mouthpiece end of the housing sleeve, the filling valve being configured to fill a heating member gas storage tank with a flammable gas;
a premix burner;
a regulating valve configured to control release of the flammable gas from the heating member gas storage tank to the premix burner; and
a mass transfer exchanger configured to heat air by heat generated from the premix burner,
wherein the mouthpiece is detachably connected to the heating member for release of the inhalable aerosol,
wherein control of the regulating valve is effected by suction on the mouthpiece,
wherein the substance depot is configured to at least partially pass combustion gases of the flammable gas, and
wherein a desired inhalation air temperature is selectable by at least a proportion of the combustion gases exiting an output of the mass transfer exchanger.

2. The device according to claim 1, wherein the suction produces a reduced pressure or a stream of air, or a reduced pressure and a stream of air.

3. The device according to claim 1, wherein the combustion gases are mixed with an excess of air comprising ambient air.

4. The device according to claim 3, wherein the desired inhalation air temperature is selectable by at least a mixing ratio of the combustion gases to the ambient air exiting an output of the mass transfer exchanger.

5. The device according to claim 4, wherein the proportion of the combustion gases or the mixing ratio of the combustion gases to the ambient air is set by regulating the mass flow of the flammable gas.

6. The device according to claim 5, wherein a reduced pressure or a stream of air, or a reduced pressure and a stream of air, regulates the mass flow of the flammable gas.

7. The device according to claim 1, wherein the flammable gas is propane gas or butane gas.

8. The device according to claim 1, wherein at least the heating member has a shape and dimensions of a cigarette or a cigar.

9. The device according to claim 1, the regulating valve comprising a regulating member and a restoring force component,
wherein the regulating member comprises a first minimally open state and a second open state,
wherein the regulating member is configured to be displaced from the first minimally open state to the second open state by the suction on the mouthpiece, and
wherein the restoring force component is configured to return the regulating member from the second open state to the first minimally open state upon stoppage of the suction on the mouthpiece.

10. The device according to claim 9, wherein the regulating member further comprises a flow section in the second open state, the flow section configured to be variably controllable between a minimally open second open state and a fully open second open state.

11. The device according to claim 1, further comprising a main valve between the heating member gas storage tank and the regulating valve, the main valve being opened by connecting the mouthpiece to the heating member and being closed by detaching the mouthpiece from the heating member.

12. The device according to claim 1, wherein at least one hot air channel leads to the at least one hot air outlet and is arranged coaxially around a longitudinal axis of the heating member gas storage tank.

13. The device according to claim 1, wherein the at least one substance in the substance depot comprises an active substance or an aroma substance, or an active substance and an aroma substance.

14. The device according to claim 13, wherein the active substance comprises nicotine, and the aroma substance comprises at least one additive of irritants, stabilisers, volatilization aids, and combinations thereof.

15. The device according to claim 13, wherein the active substance or the aroma substance, or the active substance and the aroma substance, are present in a plurality of chambers.

16. The device according to claim 1, wherein a carbon monoxide oxidation catalyst is arranged downstream of the mass transfer exchanger.

17. The device according to claim 16, wherein the carbon monoxide oxidation catalyst is a hopcalite catalyst.

18. A fuelling station for detachable connection and filling of a heating member of an aerosol-releasing inhalation device, the fuelling station comprising:
    a fuelling gas storage tank having a storage volume that is a multiple of a storage volume of a heating member gas storage tank of the heating member; and
    an outlet valve configured to connect to a filling valve of the heating member, the heating member comprising:
    a housing sleeve having at least one air inlet, and at least one hot air outlet at a mouthpiece end of the housing sleeve being separated from the at least one air inlet;
    the filling valve being disposed at the mouthpiece end of the housing sleeve and being configured to fill the heating member gas storage tank with a flammable gas;
    a premix burner;
    a regulating valve configured to control release of the flammable gas from the heating member gas storage tank to the premix burner; and
    a mass transfer exchanger configured to heat air by heat generated from the premix burner,
    wherein a mouthpiece of the aerosol-releasing inhalation device is detachably connected to the heating member and configured for release of an inhalable aerosol, the mouthpiece comprising a substance depot,
    wherein control of the regulating valve is effected by suction on the mouthpiece,
    wherein the substance depot is configured to at least partially pass combustion gases of the flammable gas, and
    wherein a desired inhalation air temperature is selectable by at least a proportion of the combustion gases exiting an output of the mass transfer exchanger.

19. The fuelling station according to claim 18, further comprising a storage cavity configured to store the heating member and at least partially enclose the outlet valve.

20. The fuelling station according to claim 19, further comprising a movable lid, the movable lid covering the storage cavity and the mouthpiece end of the housing sleeve when the movable lid is in a closed position.

21. The fuelling station according to claim 18, further comprising an ignition device.

22. The fuelling station according to claim 21, wherein the ignition device comprises a burner valve and a fuelling station burner.

23. The fuelling station according to claim 18, further comprising a fuelling gas storage tank filling valve for filling the fuelling gas storage tank.

24. The fuelling station according to claim 22, wherein the fuelling gas storage tank is divided by a piston, which is axially mobile along an adjustment path, into a first fuelling gas storage tank chamber filled with an inert gas and a second fuelling gas storage tank chamber filled with the flammable gas, and
    wherein a pressure in first fuelling gas storage tank chamber is sufficient over the adjustment path of the piston to keep the flammable gas in the second fuelling gas storage tank chamber compressed in a liquid phase.

25. The fuelling station according to claim 24, wherein the first fuelling gas storage tank chamber comprises a pressure relief valve connected to a surrounding environment.

26. The fuelling station according to claim 24, wherein the second fuelling gas storage tank chamber comprises a pressure reducer configured for connection to the outlet valve and the burner valve.

27. An aerosol-releasing inhalation apparatus, comprising:
    an aerosol-releasing inhalation device, comprising:
        a mouthpiece comprising a substance depot; and
        a heating member configured to volatilise at least one substance in the substance depot to release an inhalable aerosol, the heating member comprising:
        a housing sleeve having at least one air inlet, and at least one hot air outlet at a mouthpiece end of the housing sleeve being separated from the at least one air inlet;
        a filling valve at the mouthpiece end of the housing sleeve, the filling valve being configured to fill a heating member gas storage tank with a flammable gas;
        a premix burner;
        a regulating valve configured to control release of the flammable gas from the heating member gas storage tank to the premix burner; and
        a mass transfer exchanger configured to heat air by heat generated from the premix burner,
    wherein the mouthpiece is detachably connected to the heating member for release of the inhalable aerosol,
    wherein control of the regulating valve is effected by suction on the mouthpiece,
    wherein the substance depot is configured to at least partially pass combustion gases of the flammable gas, and
    wherein a desired inhalation air temperature is selectable by at least a proportion of the combustion gases exiting an output of the mass transfer exchanger; and
    a fuelling station for detachable connection and filling of the heating member, the fuelling station comprising:
        a fuelling gas storage tank having a storage volume that is a multiple of a storage volume of the gas tank of the heating member; and
        an outlet valve configured to connect to the filling valve of the heating member.

* * * * *